United States Patent [19]

Koiso et al.

[11] Patent Number: 4,516,564
[45] Date of Patent: May 14, 1985

[54] HEAT GENERATING BODY

[75] Inventors: Yasuhiko Koiso, Hiratsuka; Kenji Ohtsuka, Zama; Shigeo Yahara, Hiratsuka, all of Japan

[73] Assignee: Japan Pionics Co., Ltd., Tokyo, Japan

[21] Appl. No.: 417,861

[22] Filed: Sep. 14, 1982

[30] Foreign Application Priority Data

Nov. 28, 1981 [JP] Japan ................................ 56-191404

[51] Int. Cl.³ .................................................. F24J 1/00
[52] U.S. Cl. .................................... 126/263; 126/204; 128/403
[58] Field of Search ................ 126/263, 204; 128/254, 128/399, 403; 165/46; 206/439

[56] References Cited

U.S. PATENT DOCUMENTS

| 1,970,081 | 8/1934 | Eisendrath | 126/204 |
| 3,301,250 | 1/1967 | Glasser | 126/263 |
| 3,976,049 | 8/1976 | Yamashita | 126/263 |
| 4,106,478 | 8/1978 | Higashijima | 126/263 |
| 4,268,272 | 5/1981 | Taura | 126/204 |
| 4,282,005 | 8/1981 | Sato et al. | 126/204 |
| 4,366,804 | 1/1983 | Abe | 126/263 |

FOREIGN PATENT DOCUMENTS

| 0023946 | 3/1981 | Japan | 128/399 |
| 0104052 | 6/1982 | Japan | 126/204 |
| 8100092 | 8/1981 | Netherlands | 125/263 |

Primary Examiner—Samuel Scott
Assistant Examiner—Helen A. Odar
Attorney, Agent, or Firm—Koda and Androlia

[57] ABSTRACT

A heat generating body suitable for use as a body warmer or the like. The heat generating body is composed of a closed bag locally provided with at least one air permeable portion constituted by a group of fine pores of a diameter equivalent of not more than 20 microns, and a heat generating composition accommodated in the bag.

1 Claim, 2 Drawing Figures

HEAT GENERATING BODY

BACKGROUND OF THE INVENTION

The present invention relates to a heat generating body and, more particularly, to a heat generating body comprising a heat generating composition which can generate heat merely by a contact with oxygen in the air and a bag containing the heat generating composition.

Hitherto, various types of heat generating composition have been known which presents heat through a chemical reaction caused merely by a contact with air. Examples of such heat generating composition are: (1) a mixture of powders of metal such as iron, aluminum or the like and an oxidation assistant such as active carbon, electrolyte, water or the like; and (2) a mixture of a metal sulfide or polysulfide and carbonaceous material.

Such a heat generating material is packed in a container such as a bag made of an air-permeable material having an air-permeability sufficient for producing heat or a material which is inherently impermeable to air but perforated to permit air to pass therethrough. Such heat generating bodies are put into practical use as, for example, body warmers. The heat generating body is wrapped by and preserved in a material having low oxygen-permeability until it is used.

This type of heat generating body in one hand offers various advantages such as easiness and safety in use, but on the other hand suffers the following disadvantages. Namely, when this heat generating body is used as a human body warmer or as a heat source for heating mechanical equipment, parts or the like, the heat generating composition in the bag is undesirably distributed to the lower part of the bag by gravity to give quite and unnatural feel of use and to change the heat generating characteristics and reduce the amount of heat thus generated, not only when the heat generating body is subjected to a vibration or vigorous action but even when it is held stationarily.

SUMMARY OF THE INVENTION

Accordingly, it is a primary object of the invention to provide a heat generating body improved to eliminate any undesirable local distribution of the heat generating composition and to maintain the required heat generating performance for a long period of time, thereby to overcome the above-described problems of the prior art.

To this end, according to the invention, there is provided a heat generating body comprising a heat generating composition and a bag provided with at least one group of fine pores, each pore having a diameter equivalent of less than 20 microns.

This body advantageously prevents any undesirable local distribution of heat generating composition in the bag. The space inside the bag is maintained at a reduced pressure during the use. This bag, therefore, can maintain a uniform distribution of heat generating composition during the use of the heat generating body, while ensuring the supply of fresh air at a rate sufficiently large for achieving the desired temperature.

In the heat generating body of the invention, at least one group of fine pores, each pore having a diameter equivalent of an order of less than 20 microns, is provided locally in the bag containing the heat generating composition. For instance, the bag may be formed from an air-impermeable material and is locally cut to provide at one or more portions thereof to provide openings or windows which are then covered by films having fine pores of a diameter equivalent less than 20 microns (referred to simply as "microporous film", hereinafter) thereby to form the air-permeable portion. It is also possible to produce the bag by preparing a microporous film and a perforated air-impermeable film having many relative large holes of a diameter such as ranging between 0.05 and 50 mm and jointing these films to each other. In the latter case, the air-permeable portions are constituted by the apertures formed in the air-impermeable film.

In this specification, the term "diameter equivalent" is used to mean a diameter of a hypothetical circle having the same area with a sectional portion perpendicular to a hypothetical axis of the micropore and having the smallest sectional area, while the sectional portion of the micropore varies in its diameter as well as shape along the hypothetical axis thereof. The "diameter equivalent" of the micropores is measured, for example, by a bubble pressure method or by a method using a mercury porosimeter.

According to the invention, it is essential that the diameter equivalent is not more than 20 microns, for otherwise it is impossible to prevent the undesirable local distribution of the heat generating compositions. The diameter equivalent is suitably selected in accordance with the kind, quantity and the desired heat output of the heat generating composition, and preferably ranges between 0.005 and 5 microns from a practical point of view.

The microporous film used in the invention can be made, although not exclusively, from a synthetic resin such as polyethylene, polypropylene, polyfluoroethylene or the like, and the pores are formed chemically or physically in the course of the manufacture or after the manufacture of the film.

The following commercially available films are usable as the microporous film of the invention: TYVEK (manufactured by E. I. Du Pont De Nemours & Co., Inc.), DURAGARD (manufactured by Celanese Fibers Co., Ltd., U.S.A.), FP-2 (manufactured by Asahi Chemical Industry Co., Ltd., Japan), NOP (Nippon Petrochemicals Co., Ltd., Japan), NITOFLON NTF (manufactured by Nitto Electric Industrial Co., Ltd., Japan), NF SHEET (manufactured by Tokuyama Soda Co., Ltd., Japan), CELLPORE (manufactured by Sekisui Chemical Co., Ltd., Japan), GORETEX (manufactured by W. L. Gore & Associates, Inc., U.S.A.) and POLYFLON PAPER (manufactured by Daikin Kogyo Co., Ltd., Japan). There is no substantial limitation in the air-permeability of the microporous film but films having Gurley air-permeability of an order of 20 to 10,000 sec/100 ml are usable suitably.

Various films substantially impermeable to air, particularly to oxygen, can be used as the air-impermeable film. Examples of material of such films are: polyolefins such as polyethylene, polypropylene, polybutadiene or the like, synthetic resins such as polyvinyl chloride, polyvinylidene chloride, polyester, polyether, polysulfone, polyvinylon, polyamide or the like. These films can be used solely or in the form of a laminated sheet in combination with a non-woven fabric. Alternatively, a non-woven fabric coated with such synthetic resins is used as the air-impermeable film. No specific selection is imposed on the selection of the kind of non-woven fabric. For instance, a non-woven fabric of natural fibers or synthetic resin fibers such as polyamide e.g.

nylon, polyolefin or polyester are usable as the non-woven fabric in the invention.

Alternatively, the microporous film is locally or partially coated by resin material such as natural resin, synthetic resin or the like, and the air-permeable portion can be defined by non-coated portion thereof.

The total area of the air-permeable portion per bag cannot be defined strictly because it varies depending on various factors such as kind and quantity of heat generating composition, aimed temperature and duration of heat generation, as well as air-permeability of the microporous film. This total area, however, may fall within a range of between 0.2 and 40 cm$^2$ per bag which usually contains about 30 to 70 g of heat generating composition. This air-permeable portion may be formed only in one side of the bag or in both sides of the same.

Ordinary heat generating compositions adapted to generate heat upon contact with the oxygen in the air can be used as the heat generating composition used in the heat generating body of the invention. For instance, the heat generating composition may be one which makes use of an oxidation reaction of a metal such as iron, aluminum, zinc, tin or the like. It is also possible to use, as the heat generating composition, sodium sulfide, iron sulfide, sodium polysulfide and other sulfides, as well as a compound obtained in the course of oxidation such as sodium sulfite and iron sulfite. Such compositions may be used solely or, alternatively, in the form of a mixture containing such composition as the main agent and an assistant such as an electrolyte, water, filaments, silica gel, zeolite, diatom earth, active carbon or the like. The main agent and the assistant may be wrapped separately until the heat generating body is actually used or may be prepared as the mixture from the beginning. From the practical point of view, the heat generating composition preferably contains iron as the main agent.

The above and other objects, features and advantages of the invention will become clear from the following description of the preferred embodiments taken in conjunction with the accompanying drawings.

DESCRIPTION OF THE PREFERRED EMBODIMENTS

Figure 1:
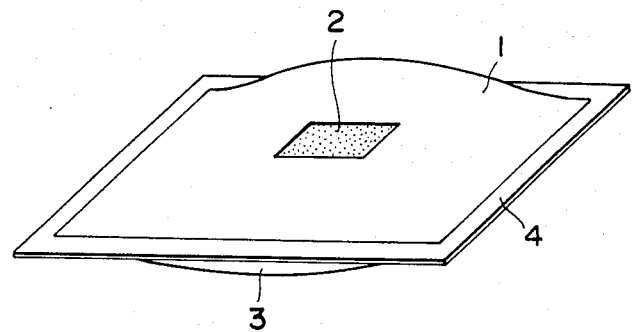
FIG. 1 is a perspective view of a heat generating body in accordance with one embodiment of the invention, in which a group of fine pores constituting an air-permeable portion is formed in one portion of a bag.

Referring first to FIG. 1 showing one embodiment of the invention, a rectangular air-impermeable film 1 is cut substantially at the central portion thereof to provide a window (not shown in the drawings). This window is covered and closed by a microporous film 2 having a size slightly greater than the size of the window to form an air-permeable portion. Then, another sheet of air-impermeable film 3 having substantially same size and shape as the first-mentioned air-impermeable film 1 is superposed to the latter, and two sheets of air-impermeable sheets 1 and 3 are jointed to each other at their peripheral edges 4 to form a bag. Then, a heat generating composition is put in the bag to complete a heat generating body of the invention.

Figure 2:
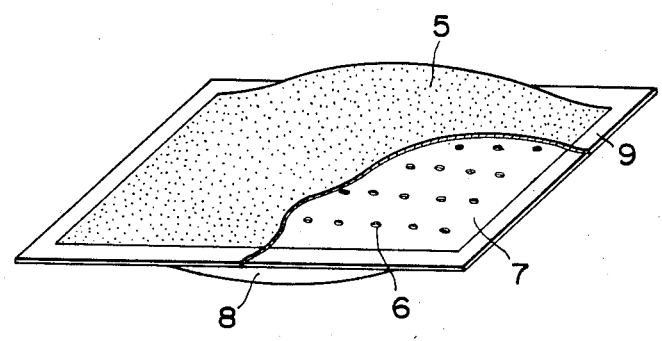
FIG. 2 is a partly cut-away perspective view of a heat generating body in accordance with another embodiment of the invention, in which groups of fine pores constituting air-permeable portions are formed in a plurality of portions of a bag.

Referring now to FIG. 2 showing another embodiment of the invention, a rectangular microporous film 5 having fine pores is laminated to a perforated air-impermeable film 7 having substantially same size and shape as the microporous film 5 and provided with a multiplicity of comparatively large holes 6 to form a laminated sheet. Then, an air-impermeable film 8 having substantially same size and shape as the rectangular microporous film 5 is superposed to the laminated sheet and is jointed to the latter at their peripheral edges 9 thereby to form a bag containing a heat generating composition to complete a heat generating body in accordance with the invention.

In the embodiments shown in FIGS. 1 and 2, the air-permeable portions are designated at numerals 2 and 6.

Although not exclusively, the bag in accordance with the invention usually has a rectangular form.

In the heat generating body as described above, the heat generating composition has to be maintained without contact with the air until it is put into practical use. To this end, the heat generating body as a whole is wrapped by an air-impermeable film or only the air-permeable portions are covered by pieces of air-impermeable film.

According to the invention, partly because the undesirable local distribution of the heat generating composition in the bag is prevented and partly because a reduced pressure is maintained within the bag, the uniform distribution of the heat generating composition is maintained so that the heat generating body as a whole is kept in the form of flexible sheet to impart a comfortable feel of use to the user. In addition, the heat generating body of the invention can maintain its heat generating performance over a long period of time.

Some practical examples of the invention will be described hereinbelow.

EXAMPLE 1

An open cell polyethylene foamed film was prepared to have a pore distribution of 0.05 to 10 microns (maximum pore diameter of 1 micron), porosity of 70%, Gurley air-permeability of 70 seconds/100 ml and a thickness of 150 microns. The polyethylene film contains calcium carbonate as a filler. Prepared also was a perforated polyethylene sheet having one hole of 0.5 mm×0.4 mm per square centimeter. The open cell polyethylene foamed film and the perforated polyethylene sheet were laminated to each other to form a laminated sheet. Two laminated sheets thus formed were then jointed to each other at their peripheral edges such that the perforated polyethylene sheets of two laminated sheets face each other, to form a bag having effective breadth and length of 85 mm and 115 mm. A heat generating composition was prepared by blending, within an atmosphere consisting of nitrogen gas, 28 g of powdered iron, 8 g of active carbon, 5 g of sodium chloride, 9 g of water and 5 g of vermiculite, and was put in the bag to complete the heat generating body of the invention.

This heat generating body was then held in contact with human body through the medium of an underwear. The heat generating body maintained a moderate temperature of about 50° C. for about 24 hours. The heat generating composition was dispersed and held in even distribution without making any undesirable local distribution, and the heat generating body as a whole was maintained in the form of flexible sheet to keep a pleasant feel of use.

EXAMPLE 2

A polypropylene microporous film was prepared to have a maximum pore diameter of 1.9 micron, Gurley air-permeability of 300 seconds/100 ml, weight of 82 g/m$^2$ and a thickness of 150 microns. This polypropylene microporous film was laminated to a perforated polyethylene sheet having one hole of 2 mm diameter per 2 cm$^2$ to form a laminated sheet. Two laminated sheets thus formed were superposed to each other such that the perforated polyethylene sheets face each other and were jointed at their peripheral edges to form a bag having effective breadth and length of 85 mm and 115 mm. The same heat generating composition as that used in Example 1 was put in the bag to complete a heat generating body in accordance with the invention.

This heat generating body was held in contact with human body through the medium of an underwear and was maintained at a moderate temperature of about 50° C. for about 24 hours. The heat generating composition was held in even distribution without making any undesirable local distribution. The heat generating body was held in a flexible sheet-like form to impart a pleasant feel of use to the user.

EXAMPLE 3

A polyethylene film was laminated to a non-woven fabric of nylon fibers to form a laminated air-impermeable sheet which thereafter was cut substantially at the center thereof to provide a window of 10 mm wide and 20 mm long. This window was covered and closed by a piece of polypropylene microporous film having a maximum pore diameter of 1.9 micron, Gurley air-permeability of 280 seconds/100 ml, and a thickness of 150 microns, thereby to form an air-permeable portion. Then, a polypropylene film substantially of the same size and shape as the laminated sheet was superposed to the laminated sheet and jointed at peripheral edges to form a bag having effective breadth and length of 85 mm and 115 mm. The same heat generating composition as that used in Example 1 was put in this bag to complete a heat generating body of the invention.

This heat generating body was held in contact with human body through the medium of an underwear and maintained a moderate temperature of about 55° C. for about 24 hours. During the use, the heat generating composition was held in even distribution without making any undesirable local distribution. The heat generating body was kept in the form of soft flexible sheet to impart a pleasant feel of use to the user.

EXAMPLE 4

A heat generating body of the invention was made by the same process as Example 3, except that the window has a size of 20 mm × 25 mm and that the piece of microporous film covering the window was made from an open cell polyethylene foamed film containing calcium carbonate having a maximum pore diameter of 1 micron, Gurley air-permeability of 70 seconds/100 ml, and a thickness of 150 microns.

This heat generating body was held in contact with the human body through the medium of an underwear and maintained a moderate temperature of about 52° C. for about 24 hours. During the use, the heat generating composition was maintained in even distribution and the heat generating body was kept in the form of a flexible sheet to impart a pleasant feel of use.

Although several preferred embodiments have been described, it is to be noted here that the described embodiments are not exclusive and various changes and modifications may be imparted thereto without departing from the scope of the invention which is limited solely by the appended claims.

What is claimed is:
1. A heat generating body comprising:
a heat generating composition for generating heat upon contact with oxygen;
a bag storing said heat generating composition, said bag comprising:
an air-permeable film with at least one window or holes, each of said holes having a diameter ranging between 0.05 and 50 mm; and
a microporous film covering and closing the window or holes, said microporous film having fine pores, each said pore having a diameter equivalent ranging between 0.005 and 5 microns; and
an outer cover with air-impermeability covering said bag, said outer cover being adapted to be removed from said bag when used.

* * * * *